US00PP10329P

United States Patent [19]

Wells

[11] Patent Number: Plant 10,329

[45] Date of Patent: Apr. 14, 1998

[54] MANDEVILLA PLANT NAMED 'MONTE'

[75] Inventor: Richard Wells, Visalia, Calif.

[73] Assignee: Monrovia Nursery Company, Azusa, Calif.

[21] Appl. No.: 621,650

[22] Filed: Mar. 26, 1996

[51] Int. Cl.[6] ..... A01H 5/00

[52] U.S. Cl. ..... Plt./54.1

[58] Field of Search ..... Plt./59.1, 68.1

[56] References Cited

U.S. PATENT DOCUMENTS

P.P. 8,479 11/1993 Henny ..... Plt./54.1

P.P. 8,842 7/1994 Henny ..... Plt./54.1

P.P. 9,117 4/1995 Christensen ..... Plt./54.1

*Primary Examiner*—Howard J. Locker

*Attorney, Agent, or Firm*—Christie, Parker & Hale, LLP

[57] ABSTRACT

A new and distinct selection of Mandevilla which shall be referred hereinafter as *Mandevilla×amabilis* cultivar Monte. *Mandevilla×amabilis* cultivar Monte differs distinctively from other *Mandevilla×amabilis* cultivars by its unique combination of pale pink buds and flowers maturing to whitish flowers which display a clear uniform pink throat distinct with yellow at the base and corolla limbs which are symmetrical presenting a full rounded flower at anthesis.

1 Drawing Sheet

BACKGROUND OF THE INVENTION

This invention relates to a new and distinct selection of *Mandevilla×amabilis* (Hort. Bach.) Dress., reputed to be a hybrid of *Mandevilla splendens×Mandevilla crassinoda* and a member of the Apocynaceae family. *Mandevilla×amabilis* cultivar Monte was the result of the seed collected in April 1990 from *Mandevilla×amabilis* cultivar Alice du Pont, and sown June 1990. In July 1992 seven seedlings were selected for flower color. The following year cultivar Monte was selected from the seven original seedlings. Selection was based on the attributes of the pale pink flowers maturing to a white color and the full rounded flower. My discovery was made at Monrovia Nursery Company, 18331 East Foothill Boulevard, Azusa, Calif. My new selection has been asexually reproduced exclusively by tissue culture since the discovery. Had this chance seedling not been discovered and propagated, it may have been lost to mankind. It is unlikely these particular select and favorable attributes of this plant could be conveyed to progeny through sexual reproduction in the next generation. In fact it was highly unusual for the parent, cultivar Alice du Pont to set seed in our southern California climate. Through extensive tissue culture propagation it has been established that the novel exceptional characteristics of this plant are stable and reliably passed on to clonal specimens through asexual reproduction.

SUMMARY OF THE INVENTION

*Mandevilla×amabilis* cv. Monte was selected for its blush pink to white flower color. Prior to my discovery only *Mandevilla×amabilis* with deep rose pink flowers were known. My selection cultivar Monte also exhibits a more refined foliage which is shorter, narrower and less bullate in texture. Cultivar Monte also exhibits a unique flower characteristics which differs from *Mandevilla×amabilis* cultivar Alice du Pont and *Mandevilla* cultivar White Delite U.S. Plant Pat. No. 8,479. The corolla limb is divided into 5 separate sections on all 3 cultivars. However, on cultivar Alice du Pont and cultivar White Delite the corolla lobes are asymmetrical. Whereas, cultivar Monte has corolla lobes which are symmetrical presenting a much more uniform rounded flower shape. My selection cultivar Monte will tolerate a 30° F. temperature which is equivalent to U.S.D.A. hardiness zone ten, but does require frost protection.

BRIEF DESCRIPTION OF ILLUSTRATION

The accompanying illustration shows flowers and foliage of specimens of 'Monte' reproduced in color as true as reasonably possible with illustrations of this type. Phenotypic expression may vary depending upon environmental and cultural conditions as well as conditions of light and temperature.

BOTANICAL DESCRIPTION

Below is a detailed description of *Mandevilla×amabilis* cultivar Monte, and when applicable comparisons of the other two cultivars. The color terminology is from The Royal Horticultural Color Charts. Comparisons of other cultivars are from containerized plants grown in similar climate/growth conditions in Azusa, Calif.

Overall habit: Tropical twining vine

Overall size: Average height of 5 meters, may achieve height to 6–7 meters. Cultivar Alice du Pont and cultivar White Delite similar in overall size.

Foliage:

*Arrangement.*—Opposite. Same for cultivar Alice du Pont and cultivar White Delite.

*Surface.*—Smooth to slightly bullate (or puckered). Cultivar Alice du Pont-deeply bullate becoming slightly bullate with maturity, cultivar White Delite-bullate maintaining condition in juvenile and mature stage.

*Secondary leaf veination.*—More secondary veins in more bullated leaf appearance; cultivar 'Monte' average 21 pairs, cultivar 'Alice duPont' average 46 pairs , cultivar 'White Delite' average 28 pairs.

*Shape.*—Lanceolate to slightly obovate — elliptic. Cultivar Alice du Pont — elliptic-oblong. Cultivar White Delite — elliptic.

*Size.*—10–14 cm long; 5–7 cm wide. Cultivar Alice du Pont 15 –18 cm long; 8–10.5 cm wide. Cultivar White Delite 11–12.5 cm long; 5–6 cm wide.

*Leaf length to width ratio.*—Foliage will vary in size due to growing conditions, however, the more reliable length to width ratio should be consistent in various climate regions. Cultivar Monte — 2. Cultivar Alice du Pont — 1.5 to 1.7, the widest leaf.

Cultivar White Delite — 2.1 to 2.2, the narrowest leaf.

*Color of juvenile foliage.*—Upper surface: Green Group 144A. Lower surface: Green Group 143C with tinge of Red Group 53A.

*Color of mature foliage.*—Upper surface: Green Group 139A. Lower surface: Green Group 138A. Midrib: Green Group 144D.

*Texture.*—Coriaceous all 3 cultivars.

Flowers:

*Arrangement.*—Axillary racemes all 3 cultivars.

*Bloom season.*—Flowers produced Spring through Fall all 3 cultivars.

*Corolla diameter.*—9 to 12 cm. Cultivar Alice du Pont — 9.5–12 cm. Cultivar White Delite — 8–10 cm.

*Corolla lobes.*—5 in number widely obovate in shape with a short acuminate tip symmetrically centered at the end of the tip. The cultivars 'Alice duPont' and 'White Delite' both have asymmetrical lobes, the overlapping margin is rounded the opposite margin underneath neighboring lobe is straight ending in an abrupt acuminate tip which is not centrally located on the lobe.

*Corolla tube length.*—From base of calyx to corolla 4.0 cm to 5.0 cm.

*Stamens.*—5 in number, borne on corolla.

*Style.*—Twice as long as calyx lobes.

*Calyx lobes.*—5 in number 5–8 mm in length.

*Petiole length.*—5 mm to 13 mm. Flowers last at least 3 to 5 days.

*Fragrance.*—Light delicate fragrance.

*Margins.*—Smooth and entire.

*Corolla shape at anthesis.*—The corolla lobes overlap fully with only a space of 5 to 10 mm difference in depth where the lobes overlap. Cultivar Alice du Pont and White Delite both display a definite deep cut of 10 mm to 20 mm between the lobes due to asymmetrical lobes with straight margin overlapped by rounded margin.

*Color.*—Determined in early June with temperatures ranging from 70° F. night temperature to high 80° F. day temperatures for the last 20 days. It is believed cooler night temperatures promote more pink shades in flowers and warm night temperatures more white shades in flowers. The color of Cultivar Monte initially is Red Group 56D mixed with Red-Purple Group 62C and 62D and White Group 155C. As flower matures White Group 155B becomes more prominent. The corolla throat is Red Group 56A and does not appear to fade with age. The base of the inner throat is Yellow Group 3D and does not appear to fade with age. The corolla color of Cultivar Alice du Pont is Red-Purple Group 63C with Red-Purple 63B within the throat. Base of throat is White Group 155A with no yellow displayed. The corolla color of Cultivar White Delite is Red-Purple Group 62D. The pink color does fade and White Group 155D does become more promient, however, Red Purple Group 62D is present on the corolla. The throat is Red-Purple Group 62C mixed with Green-Yellow Group 1C, prominently the base displays Green-Yellow Group 1C. This is an identification difference as my selection Cultivar Monte has a clear cut distinct line of yellow at the base and striated pink throat whereas Cultivar White Delite has the clear yellow base but the yellow is mixed with the striated pink within the throat.

*Fruit.*—To date my new selection has not produced fruit.

I claim:

1. A new variety of Mandevilla plant substantially as herein shown and described.

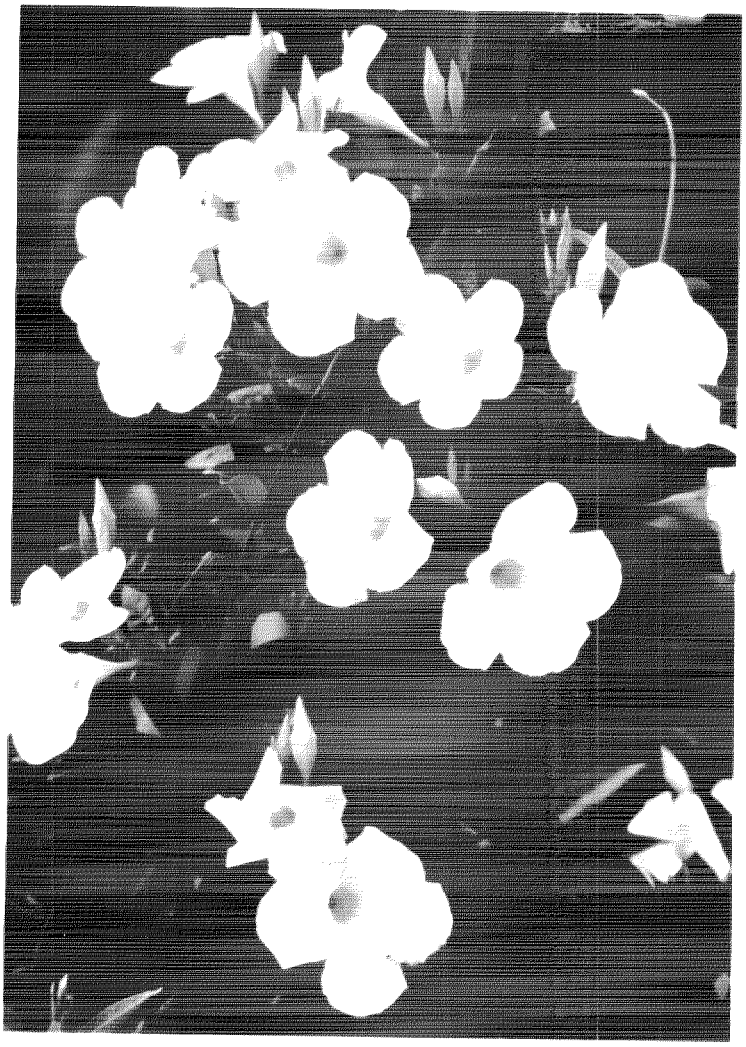

* * * * *